US00PP36854P2

(12) United States Plant Patent
Hansen

(10) Patent No.: US PP36,854 P2
(45) Date of Patent: Jul. 22, 2025

(54) ***HOSTA* PLANT NAMED 'Out of Time'**

(50) Latin Name: ***Hosta* hybrid (Tratt.)**
Varietal Denomination: Out of Time

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 18/831,121

(22) Filed: Jul. 25, 2024

(51) Int. Cl.
*A01H 6/12* (2018.01)
*A01H 5/12* (2018.01)

(52) U.S. Cl.
USPC ..... Plt./353

(58) Field of Classification Search
USPC ..... Plt./263.1, 353
See application file for complete search history.

*Primary Examiner* — Karen M Redden

(57) ABSTRACT

A new and distinct *Hosta* plant named 'Out of Time' of arching, lanceolate, variegated leaves having a lustrous underside and moderately wavy margins. The foliage has deep green centers and yellowish-chartreuse margins that mature to creamy-white in high light exposure. The flowers are purplish and remain closed until dropping. 'Out of Time' has excellent, small, compact, mounded habit and is useful in the landscape, in containers, as a specimen, or en masse.

2 Drawing Sheets

Botanical classification: *Hosta* hybrid (Tratt.).
Variety denomination: 'Out of Time'.

STATEMENT REGARDING PRIOR DISCLOSURES UNDER 37 CFR 1.77(b)(6)

No plants of *Hosta* 'Out of Time' have been sold, in this country or anywhere in the world, nor has any disclosure of the new plant been made, more than one year prior to the filing date of this application.

BACKGROUND AND ORIGIN OF THE PLANT

The present invention relates to a new and distinct *Hosta* plant, *Hosta* 'Out of Time' hereinafter also referred to as the new plant or by the cultivar name, 'Out of Time'. *Hosta* 'Out of Time' was discovered on Feb. 14, 2023, by the inventor as a whole plant mutation of 'Time in a Bottle' U.S. Plant Pat. No. 33,267 at a wholesale perennial nursery in Zeeland, Michigan, USA. The new plant was assigned the breeder code 23-SP-HOST-1205 and passed the initial evaluation in the summer of 2023. It has been asexually propagated by division at the same nursery since 2023 with the resultant asexually propagated plants having retained all the same traits as the original plant.

There are over 7,000 registered and unregistered *Hostas* with The American *Hosta* Society, which is the International Cultivar Registration Authority for the genus *Hosta*. Some of these have chartreuse leaf blades with wavy margins.

The most similar *Hosta* cultivars known to the applicant are 'Alakazaam' U.S. Plant Pat. No. 22,342, 'August Fire' (not patented), 'Frenzy' (not patented); 'Indy Parade Lap' (not patented), 'Pineapple Punch' U.S. Plant Pat. No. 18,318, and 'Sandhill Crane' (not patented).

'Alakazaam' has a smaller habit and smaller foliage, the leaves are less arching, have a wider and lighter margin, and have more sinuate margins. 'August Fire' has a larger habit and larger foliage, the leaves are broader with a more oblong ovate blade, and the margin is more creamy-colored.

'Frenzy' has larger habit with larger and broader foliage, the upper surface is more lustrous, the apex has a distinctive curve, and it lacks the reddish spotting of the petiole. 'Pineapple Punch' is larger in habit and foliage size, the leaf blades are slightly wider with more sinuate margins, and the petioles lack the extensive reddish spotting. 'Sandhill Crane' has a flatter leaf without the sinuate margins, the variegated margin is more creamy-colored, and it lacks the reddish spotting on the petiole. Each of the above comparison cultivars have flowers that open at maturity, whereas the new plant has flowers that remain closed.

The parent has foliage that is solid chartreuse without the green margin.

Other *Hosta* cultivars may have traits similar to 'Out of Time' but the new plant differs from the above listed cultivars and all other *Hostas* known to the applicant, by the combination of the following traits.

1. Leaves are small-sized, lanceolate, with narrowly acute apices and attenuate base;
2. Arching leaves have a moderately wavy margin;
3. Variegated leaves have deep green centers and yellowish-chartreuse margins that become creamy-white with maturity;
4. Underside of leaf lustrous;
5. Petiole develops a strong reddish spotting;
6. Flowers are purplish and remain closed until dropping;
7. Compact mounded habit and useful in the garden as edging or front border, in containers, as a specimen or en masse.

BRIEF DESCRIPTION OF THE DRAWING

The photograph of the new plant demonstrates the overall appearance of the new plant including the unique traits. The colors are as accurate as reasonably possible with color reproductions. Ambient light spectrum, temperature, source, and direction may cause the appearance of minor variation in color.

The drawings show a two-year-old plant in a partially shaded display garden at a nursery in Zeeland, MI with supplement fertilizer and water as needed.

Figure 1:
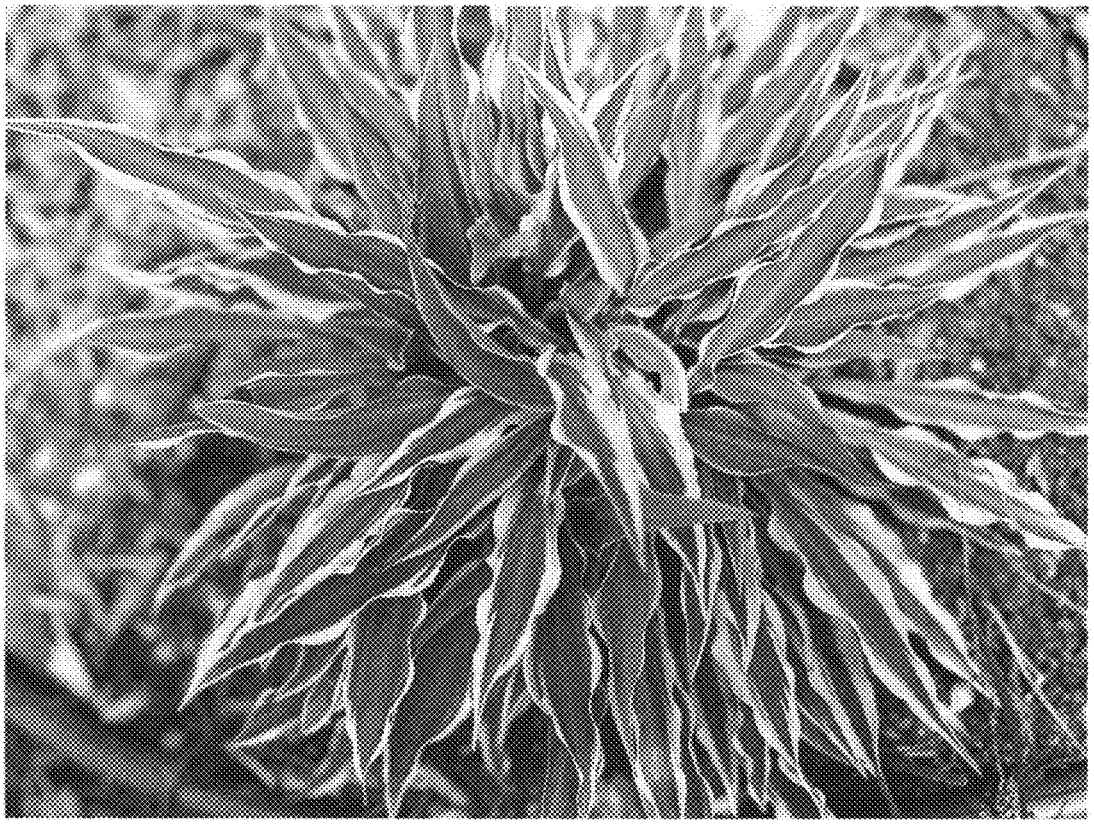
FIG. 1 shows a view of the plant from above.
Figure 2:
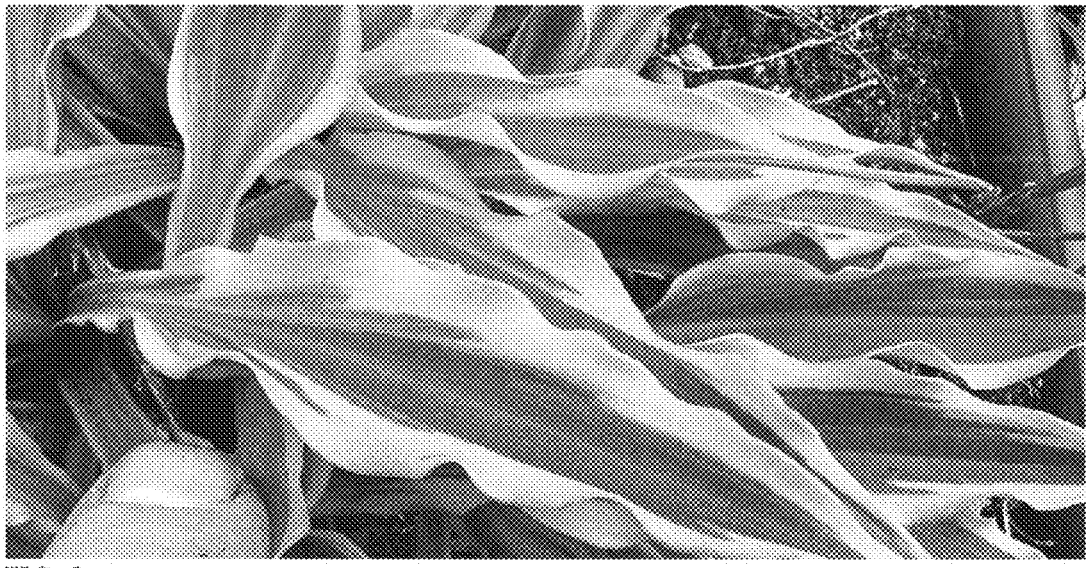
FIG. 2 shows a close-up of young and mature foliage with reddish spots on the petioles.
Figure 3:
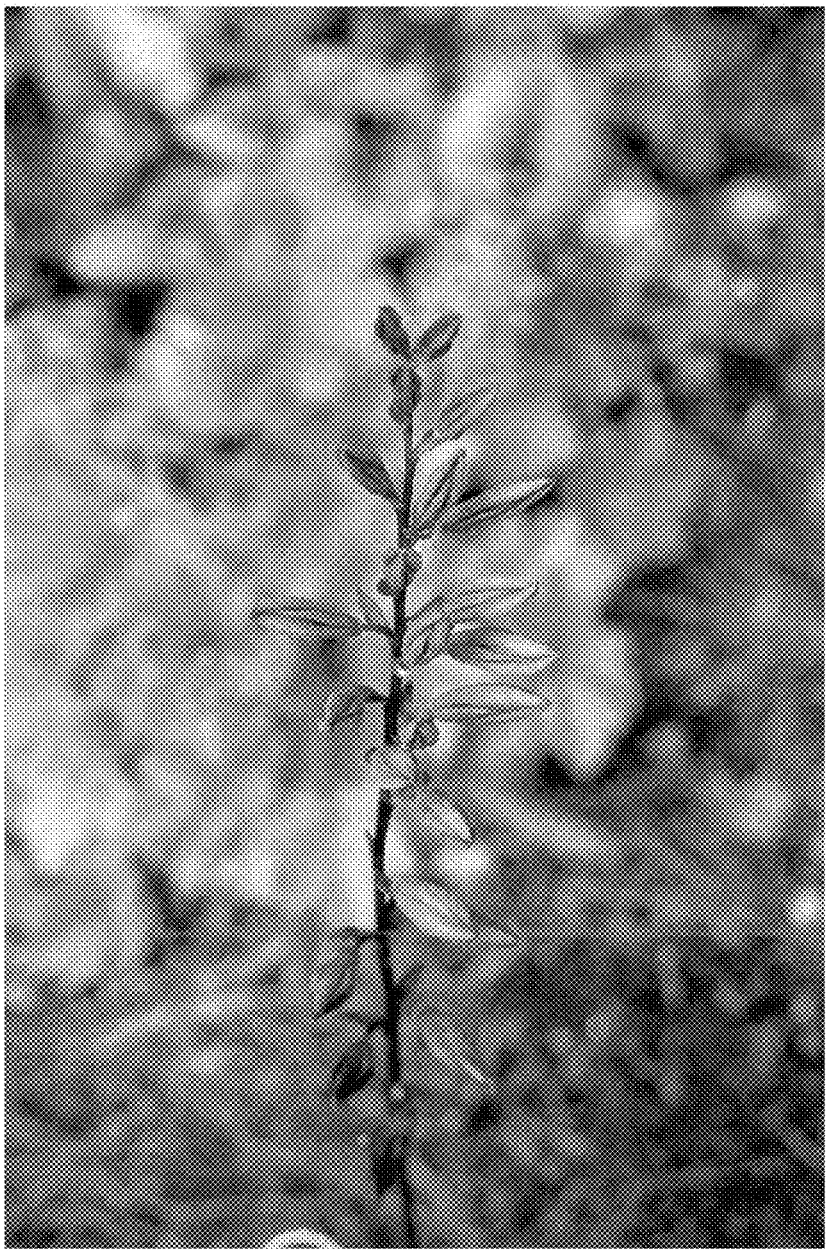
FIG. 3 shows a close-up of the scape with mature unopened flowers and buds.

DETAILED BOTANICAL DESCRIPTION.

The following descriptions and color references are based on the 2015 edition of The Royal Horticultural Society Colour Chart except where common dictionary terms are used. The new plant, *Hosta* 'Out of Time', has not been observed under all possible environments. Those skilled in the art will appreciate that certain characteristics will vary with plants that are more mature or plants that are less mature. The phenotype may vary slightly with different environmental conditions, such as temperature, light, fertility, moisture, and maturity levels, but without any change in the genotype. The following observations and size descriptions are of a two-year-old plant in a shaded trial garden in Zeeland, Michigan with supplemental water and fertilizer:

Botanical classification: *Hosta* x hybrid;

Parentage: Whole plant mutation of 'Time in a Bottle';

Propagation: Garden division;

Time to initiate roots from tissue culture: About two weeks;

Growth rate: Moderately vigorous;

Crop time: About three months to finish during the spring in a one-liter container from rooted tissue culture plantlet;

Rooting habit: Fleshy, lightly branching;

Root color: Nearest RHS NN155C when actively growing;

Plant shape and habit: Hardy herbaceous perennial with basal rosette of leaves emerging from rhizomes producing a short, compact, mound of arching petioles and leaves; with four divisions having about 10 to 11 leaves per division;

Plant size: Foliage height about 17 cm above soil line to the top of the leaves and about 37 cm wide at the widest point at the soil line;

Foliage description: Lanceolate; narrowly acute apex, attenuate base; margin entire, moderately sinuate; flexible; smooth, without blistering, dimpling, or bulging; glabrous and dull adaxial and glabrous and slightly lustrous abaxial;

Leaf blade size: To about 13.5 cm long and 2.6 cm wide; average about 12 cm long and 2.4 cm wide; variegated margin to about 4 mm wide with an average about 3 mm wide above and average about 2.5 mm wide below;

Leaf blade color: Young adaxial center between RHS 146D and RHS N144D, adaxial margin abaxial between RHS 150B and RHS 150C, with an intermediate region between center and margin of nearest RHS 145A; young abaxial center between RHS 146D and RHS 145B, and abaxial margin RHS 145C and RHS 150C, without noticeable intermediate region; mid-season and later in heavy shade adaxial center nearest RHS NN137B, adaxial margin between RHS N144A and RHS 146D, with intermediate region between center and margin of mid-season between RHS 138C and RHS 138B; midseason and later in heavy shade abaxial center between RHS 137B and RHS NN137B, margin between RHS 144A and RHS N144A, with intermediate region between center and margin between RHS 147C and RHS 146D; mid-season and later in high light adaxial center nearest RHS 137A, adaxial margin nearest RHS 4D, intermediate region comprising RHS 147C, RHS 144A, and RHS 148B; mid-season and later in high light abaxial center between RHS 137B and RHS N137C, margin nearest RHS 4D, and intermediate region comprising RHS 145A and RHS 147B;

Petiole: Glabrous adaxial and abaxial; dull adaxial, slightly lustrous abaxial; shallowly concavo-convex; flexible; to 6 cm long, 9 mm wide at base and 3 mm deep; average about 5.5 cm long and 8 mm wide; maculate with spots on adaxial and abaxial between 0.2 mm and 1 mm diameter;

Petiole color: Young adaxial and abaxial center nearest RHS 145B and heavily maculate with spots of nearest RHS 183A more densely concentrated proximally and less concentrated distally, young adaxial and abaxial margin nearest RHS 145C sparsely maculate with spots nearest RHS 183C; mature adaxial center nearest RHS 137A with heavily maculate with spots of nearest RHS 183A more densely concentrated proximally and less concentrated distally, mature abaxial center nearest RHS 193B and densely maculate with nearest RHS 183A to nearly solid proximally decreasing distally, mature adaxial and abaxial margin between RHS 146D and RHS 145A sparsely maculate with spots nearest RHS 183A, mature adaxial and abaxial intermediate region between center and margin not distinguishable;

Veins: Typically, up to five pairs and midrib; parallel; glabrous adaxial and abaxial; smooth on adaxial and slightly costate abaxial;

Veins color: Adaxial center nearest RHS NN137B proximally and nearest RHS 146B distally, adaxial margin nearest RHS 146D, abaxial center between RHS 146C and RHS 147C and margin nearest RHS 146C;

Flower description:

Buds one to two days prior to maturity: Elongated ovoid; acute apex; base cordate to reflexed around distal 1 mm of pedicel; about 45 mm long and 8 mm in diameter near the middle; no restricted tube or tapered portion;

Bud color: Between RHS 85A and RHS N87D;

Inflorescence: Cylindrical; glabrous; slightly lustrous; to about 59 cm long and 3 mm diameter at base; aspect leaning at about a 45-degree angle; with about 24 flowers in the terminal 27 cm; to about 7 cm wide; flowers distinctly secund;

Flowers: Perfect; incomplete; remaining closed through dehiscence; aspect mostly horizontal, slightly downwardly; to 30 mm long, 9 mm diameter near middle, tapering to 4 mm diameter at base;

Flower lasting: Persists for about three days following maturity; scapes remain effective with flowers beginning mid-August for about four weeks; with about 44 flowers per scape; no detectable fragrance;

Flowering period: Scapes remain effective with flowers beginning late July to early August for about three weeks; with about 24 flowers per scape;

Flower fragrance: No detectable fragrance;

Tepals: Two nearly identical sets of three, glabrous; lanceolate; entire margins; narrowly acute apices, about 30 mm long and fused in the basal 13 mm;

*Inner set*.—Approximately 6 mm wide slightly above fusion point.

*Inner set color*.—Adaxial nearest RHS 79C; abaxial outer edge nearest RHS N82D, central portion including tube nearest RHS 83D.

*Outer set*.—Approximately 6 mm wide slightly above fusion point.

*Outer set color*.—Adaxial nearest RHS 79C; abaxial between RHS 83D and RHS 83C.

Gynoecium: One to seven per flower; to 24 mm long; superior;

*Style*.—One larger central style surrounded by up to 6 thinner styles; cylindrical; thinner outer styles twisted and distortedly bent; variable; inner style to about 15 mm long and 1 mm diameter, outer styles to about 26 mm long and 0.5 mm diameter; color nearest RHS 145D.

*Stigma*.—Puberulent; rounded; variable; about 1 mm to 0.5 mm across and 0.5 mm tall; color nearest RHS NN155A.

*Ovary*.—Ovoidal; superior; apex truncate; base truncate; to about 4 mm long and 3.5 mm diameter in middle; color apex and base nearest RHS N79A, with longitudinal lines of nearest RHS 145B.

Androecium: Not observed;

*Filaments*.—Not observed.

*Anthers*.—Not observed.

*Pollen*.—Not observed.

Peduncle: Cylindrical; usually one per mature division; about 4 per plant; glabrous; moderately glaucous; arching to leaning with maturity; to about 59 cm tall, and about 3 mm in diameter at base, average about 57 cm tall and 3 mm diameter at base;

Peduncle color: Variable, when flowering nearest RHS N138C; after flowering season proximally between RHS 145A and RHS 192B, distally nearest RHS 196D;

Pedicel: Cylindrical; glabrous; slightly lustrous; curved slightly downward; to about 15 mm long and 1 mm diameter, decreasing in length distally;

Pedicel color: Nearest RHS 147B with a moderate blush nearest and RHS 86B;

Floral bracts: Each flower normally subtended by a single bract; lanceolate; narrowly acute apex and truncate clasping base; entire margin; strongly concavo-convex; glabrous and slightly glaucous abaxial and adaxial; to about 15 mm long 4 mm wide, decreasing distally; one proximal bract about 6 cm below first flower, about 50 mm long and 20 mm across, Proximal bract: One proximal bract about 6 cm below first flower; about 50 mm long and 20 mm across; ovate; with acute apex and cuneate base; color adaxial and abaxial margin between RHS 146D and RHS N144A, color adaxial and abaxial center nearest RHS NN137D;

Floral bract color: Proximal bracts at time of flowering adaxial and abaxial longitudinal center between RHS 145D and RHS 160D and margins nearest RHS 86C;

Fruit: Not observed;

Seeds: Not observed;

Disease resistance: The thick glaucous leaves provide some resistance to slug feeding. Other resistance to pests (including: Odocoileus virginianus and Oryctotagus cuniculus) and diseases common to *Hostas* is equal that typical of other cultivars. The plant grows best and shows the best coloration with plenty of moisture, adequate drainage, and light shade, but the new plant is able to tolerate some drought when mature.

Hardiness at least from USDA zone 3 through 8, and other disease resistance is typical of that of other *Hostas*.

It is claimed:

1. A new and distinct *Hosta* plant cultivar named *Hosta* 'Out of Time' as herein described and illustrated.

* * * * *